(12) United States Patent
Ponzi

(10) Patent No.: US 6,210,362 B1
(45) Date of Patent: *Apr. 3, 2001

(54) STEERABLE CATHETER FOR DETECTING AND REVASCULARING ISCHEMIC MYOCARDIAL TISSUE

(75) Inventor: Dean M. Ponzi, Glendora, CA (US)

(73) Assignee: Cordis Webster, Inc., Diamond Bar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/255,691

(22) Filed: Feb. 23, 1999

Related U.S. Application Data

(63) Continuation of application No. 08/924,622, filed on Sep. 5, 1997, now abandoned.

(51) Int. Cl.$^7$ .................................................. A61M 37/00
(52) U.S. Cl. .......................................................... 604/95.01
(58) Field of Search ............................ 604/95.01, 95.02, 604/95.04, 95.05; 600/103, 139, 156, 160, 188; 607/6; 128/642, 658, 662.06

(56) References Cited

U.S. PATENT DOCUMENTS

| | | |
|---|---|---|
| Re. 34,502 | 1/1994 | Webster, Jr. .......................... 607/125 |
| 4,662,368 | 5/1987 | Hussein et al. ....................... 128/303 |

(List continued on next page.)

FOREIGN PATENT DOCUMENTS

WO965469   11/1996   (WO) .

OTHER PUBLICATIONS

Aretz, et al., "Intraluminal ultrasound guidance of transverse laser atherectomy", SPIE, Vol. 1201, 1990, pp. 68–78.

Hardy et al., "A Histologic Study of Laser–Induced Transmyocardial Channels", Lasers in Surgery and Medicine, vol. 6, 1987, pp. 563–573.

(List continued on next page.)

*Primary Examiner*—Sharon Kennedy
*Assistant Examiner*—Ann Y. Lam
(74) *Attorney, Agent, or Firm*—Christie, Parker & Hale, LLP

(57) ABSTRACT

A steerable, direct myocardial revascularization catheter comprises a catheter body, a control handle, a tip section, and a means for deflecting the tip section by manipulation of the control handle. The catheter body has an outer walls proximal and distal ends and at least one lumen extending therethrough. The control handle is situated at the proximal end of the catheter body. The tip section comprises a flexible tubing having proximal and distal ends and at least one lumen extending therethrough. The proximal end of the tip section is fixedly attached to the distal end of the catheter body.

The catheter also comprises an electromagnetic sensor in the distal portion of the tip section for producing electrical signals indicative of the location of the electromagnetic sensor. An electromagnetic sensor cable is electrically connected to the electromagnetic sensor and extends through the tip section, catheter body and control handle for carrying electrical signals from the electromagnetic sensor to a circuit board located in the control handle.

The catheter further comprises an optic fiber having a distal end and a proximal end. The optic fiber extends through the control handle, a lumen in the catheter body and a lumen in the tip section. The distal end of the optic fiber is substantially flush with the distal end of the tip section.

29 Claims, 8 Drawing Sheets

U.S. PATENT DOCUMENTS

| | | | |
|---|---|---|---|
| 4,753,223 | * 6/1988 | Bremer | 604/95 X |
| 4,785,815 | 11/1988 | Cohen | 128/642 |
| 4,788,975 | 12/1988 | Shturman et al. | 128/303.1 |
| 4,790,310 | 12/1988 | Ginsburg et al. | 128/303.1 |
| 4,834,093 | 5/1989 | Littleford et al. | 128/303.1 |
| 4,844,062 | 7/1989 | Wells | 128/303.1 |
| 4,850,351 | 7/1989 | Herman et al. | 128/303.1 |
| 4,860,743 | 8/1989 | Abela | 128/303.1 |
| 4,862,887 | 9/1989 | Weber et al. | 128/303.1 |
| 4,890,898 | 1/1990 | Bentley et al. | 350/96.23 |
| 4,913,142 | 4/1990 | Kittrell et al. | 606/7 |
| 4,917,084 | 4/1990 | Sinofsky | 606/7 |
| 4,967,745 | 11/1990 | Hayes et al. | 128/303.1 |
| 4,993,412 | 2/1991 | Murphy-Chutorian | 606/7 |
| 4,997,431 | 3/1991 | Isner et al. | 606/15 |
| 4,998,916 | 3/1991 | Hammerslag et al. | 604/95 |
| 5,111,832 | 5/1992 | Saksena | 128/898 |
| 5,125,924 | 6/1992 | Rudko | 606/12 |
| 5,125,926 | 6/1992 | Rudko et al. | 606/19 |
| 5,188,634 | 2/1993 | Hussein et al. | 606/14 |
| 5,203,772 | 4/1993 | Hammerslag et al. | 604/95 |
| 5,242,437 | 9/1993 | Everett et al. | 606/15 |
| 5,242,441 | 9/1993 | Avitall | 606/41 |
| 5,263,952 | 11/1993 | Grace et al. | 606/15 |
| 5,281,212 | 1/1994 | Savage et al. | 606/15 |
| 5,318,525 | 6/1994 | West et al. | 604/95 |
| 5,368,564 | 11/1994 | Savage | 604/95 |
| 5,380,316 | 1/1995 | Aita et al. | 606/7 |
| 5,389,096 | 2/1995 | Aita et al. | 606/15 |
| 5,391,199 | 2/1995 | Ben-Haim | 607/122 |
| 5,423,805 | 6/1995 | Brucker et al. | 606/15 |
| 5,429,604 | 7/1995 | Hammersmark et al. | 604/95 |
| 5,431,168 | 7/1995 | Webster, Jr. | 128/658 |
| 5,439,000 | 8/1995 | Gunderson et al. | 128/664 |
| 5,443,489 | 8/1995 | Ben-Haim | 607/115 |
| 5,454,370 | 10/1995 | Avitall | 128/642 |
| 5,462,544 | 10/1995 | Saksena et al. | 606/15 |
| 5,489,270 | 2/1996 | van Erp | 604/95 |
| 5,500,012 | 3/1996 | Brucker et al. | 607/122 |
| 5,505,725 | 4/1996 | Samson | 606/7 |
| 5,514,128 | 5/1996 | Hillsman et al. | 606/7 |
| 5,546,951 | 8/1996 | Ben-Haim | 128/702 |
| 5,549,542 | 8/1996 | Kovalcheck | 600/146 |
| 5,554,152 | 9/1996 | Aita et al. | 606/7 |
| 5,555,883 | 9/1996 | Avitall | 128/642 |
| 5,558,091 | 9/1996 | Acker et al. | 128/653.1 |
| 5,568,809 | 10/1996 | Ben-haim | 128/656 |
| 5,591,159 | 1/1997 | Taheri | 606/15 |
| 5,607,421 | 3/1997 | Jeevanandam et al. | 606/15 |
| 5,617,854 | 4/1997 | Munsif | 128/642 |
| 5,636,634 | 6/1997 | Kordis et al. | 128/642 |
| 5,666,970 | 9/1997 | Smith | 128/772 |
| 5,715,832 | 2/1998 | Koblish et al. | 128/754 |
| 5,730,704 | 3/1998 | Avitall | 600/374 |
| 5,755,760 | 5/1998 | Maguire et al. | 607/122 |
| 5,843,076 | * 12/1998 | Webster, Jr. et al. | 604/41 |
| 6,027,473 | * 2/2000 | Ponzi | 604/95 |

OTHER PUBLICATIONS

Jeevanandam et al., "Myocardial Revascularization by Laser-Induced Channels", Surgical Forum, pp. 225–227.

Lee et al., "Effects of laser irradiation delivered by flexible fiberoptic system on the left ventricular internal myocardium", Brief Communications, pp. 587–590.

Mirhoseini et al., "Clinical and Histological Evaluation of Laser Myocardial Revascularization", Journal of Clinical Laser Medicine & Surgery, Jun. 1990, pp. 73–78.

Mirhoseini et al., "Clinical Report: Laser Myocardial Revascularization", Lasers in Surgery and Medicine, vol. 6, 1986, pp. 459–461.

Mirhoseini et al., "Laser applications in thoracic and cardiovascular surgery", Medical Instrumentation, vol. 17, 1983, 4 pages.

Mirhoseini et al., "Lasers in Cardiothoracic Surgery", pp. 216–232.

Mirhoseini et al., "Myocardial Revascularization by Laser: A Clinical Report", Lasers in Surgery and Medicine, vol. 3, 1983, pp. 241–245.

Mirhoseini et al., "New Concepts in Revascularization on the Myocardium", Ann Thorac Surg., vol. 45, 1988, pp. 415–420.

Mirhoseini et al., "Revascularization of the Heart by Laser", Journal of Microsurgery, vol. 2, 1981, pp. 253–260.

Oz et al., "A Fiberoptic Compatable Midinfrared Laser with $CO_2$ Laser–Like Effect: Application to Atherosclerosis", Journal of Surgical Research, vol. 47, 1989, pp. 493–501.

Treat et al., "Preliminary Evaluation of a Pulsed 2.15–$\mu$m Laser System for Fiberoptic Endoscopic Surgery", Lasers in Surgery and Medicine, vol. 8, 1988, pp. 322–326.

Yano et al., "Prevention of Acute Regional Ischemia With Endocardial Laser Channels", The Society of Thoracic Surgeons, vol. 56, 1993, pp. 46–53.

* cited by examiner

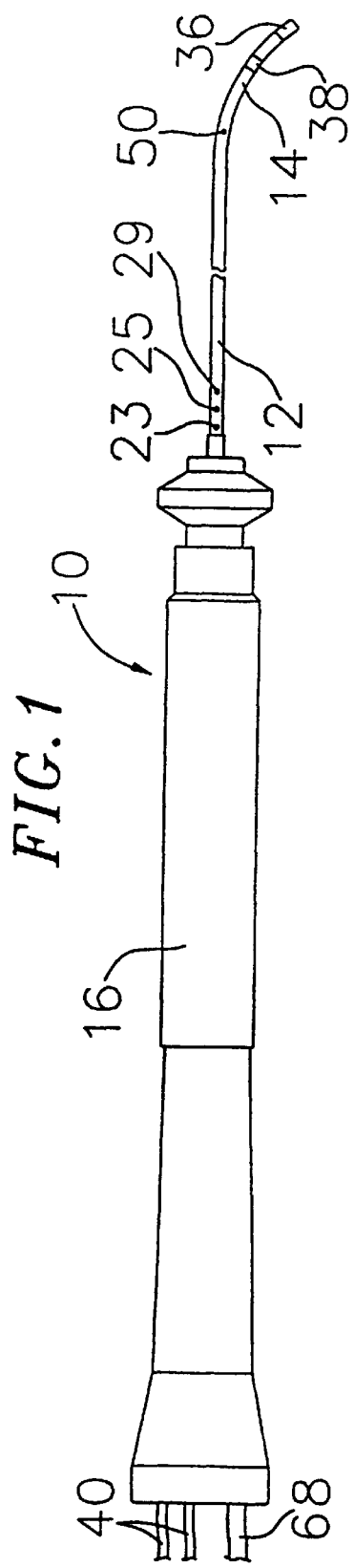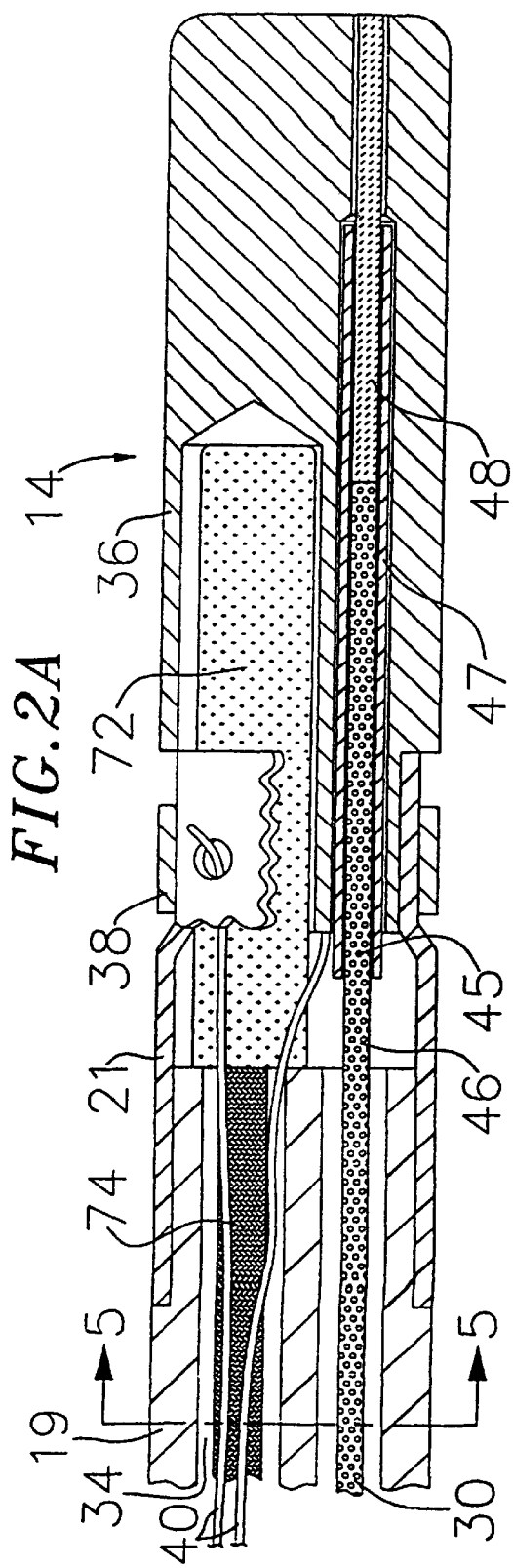

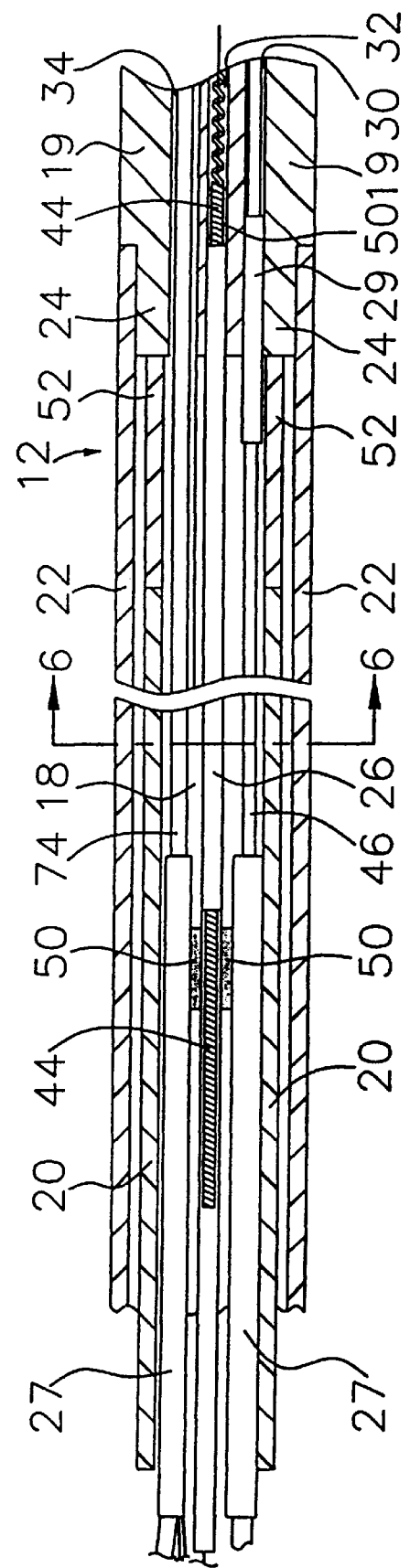

STEERABLE CATHETER FOR DETECTING AND REVASCULARING ISCHEMIC MYOCARDIAL TISSUE

This application is a continuation of application Ser. No. 08/924,622, filed Sep. 5, 1997, now abandoned.

FIELD OF THE INVENTION

The present invention relates to steerable catheters which are particularly useful in direct myocardial revascularization procedures.

BACKGROUND OF THE INVENTION

Direct myocardial revascularization (DMR), also referred to as percutaneous myocardial revascularization, is a technique that allows physicians to treat patients who have sustained a myocardial infraction by burning channels in the myocardium that has been determined to be ischemic heart tissue. The channels, which are burned by a laser, allow for angiogenesis, i.e., the formation of blood vessels.

Several myocardial revascularization procedures are known that require that the chest wall be opened to access the heart muscle with laser devices. The procedures are not very desirable, as they require major surgery that can result in severe complications. Aita et al., U.S. Pat. No. 5,389,096, describes a procedure for performing myocardial revascularization percutaneous by inserting a guidable elongated flexible lasing apparatus, such as a catheter, into a patient's vasculature. The distal end of the catheter is guided to an area in the heart to be revascularized. The inner wall of the heart is then irradiated with laser energy to cause a channel to be formed from the endocardium into the myocardium.

For obvious reasons, DMR catheters require the physician to have more control and information than other catheters having an optic fiber, such as ablation catheters. Aita et al. generally describes a DMR catheter. The present invention is directed to an improved DMR catheter which allows the physician to have greater control and obtain more information than the catheter described in Aita el al.

SUMMARY OF THE INVENTION

The present invention provides a steerable catheter particularly useful in DMR procedures used to treat ischemic heart tissue. The steerable DMR catheter comprises a catheter body or shaft, a tip section attached to the distal end of the catheter body and a control handle attached to the proximal end of the catheter body. A puller wire is anchored at its proximal end in the control handle and extends through a lumen in the catheter body and a lumen in the tip section and is anchored at or about the distal end of the tip section. Manipulation of the control handle results in deflection of the tip section. An optic fiber suitable for transmission of laser energy extends through the control handle, catheter body and tip section, the distal end of the optic fiber being generally flush with the distal end surface of the tip section. The proximal end of the optic fiber extends proximally from the control handle to a suitable connector which connects the optic fiber to a source of laser energy. The optic fiber is used to transmit laser energy for creating channels, i.e. blind holes, in the heart tissue which induces revascularization.

In a preferred embodiment of the invention, the tip section of the DMR catheter comprises an electromagnetic sensor. The electromagnetic sensor is connected to a circuit board by means of a sensor cable which extends proximally through the tip section, catheter body, and control handle. The circuit board is preferably housed in the handle. Signals from the circuit board are transmitted through a cable to a computer and monitor. The electromagnetic sensor allows a physician to create a visual representation of the heart chamber and to view the location of the sensor, and therefore the catheter tip, within the chamber.

In another preferred embodiment, the DMR catheter comprises a tip electrode and one or more ring electrodes spaced proximally from the tip electrode. Each electrode is connected by means of electrode lead wires which extend through the tip section, catheter body and control handle to an appropriate connector, and from there, to a suitable monitor. The tip and ring electrodes allow the electrical activity of the heart tissue to be mapped. In a particularly preferred embodiment of the invention, the DMR catheter comprises both an electromagnetic sensor within the tip section and a tip electrode and one or more ring electrodes. This combination allows a physician to map the electrical activity of the heart wall of a particular chamber, e.g., the left ventricle, by means of the tip and ring electrodes to determine ischemic areas and simultaneously to record the precise location of the tip section within the heart by means of the electromagnetic sensor to create a three-dimensional representation of the heart chamber which is displayed visually on a monitor. Once an ischemic area has been mapped, the tip section is moved to that area and deflected to allow the optic fiber to be generally normal to the heart wall, and then laser energy is transmitted onto the heart tissue for creating a channel within the heart tissue.

In another aspect of the invention, the optic fiber comprises a protective jacket, preferably made out of aluminum. The optic fiber extends through the control handle and catheter body and into the tip section which carries a tip electrode. In the tip section, the optic fiber extends through an optic fiber lumen in the tip electrode, the distal end of the optic fiber being flush with the distal face of the tip electrode. The aluminum jacket is removed from the distal portion of the optic fiber which extends through the tip electrode. This removal avoids the possibility that particles of the aluminum jacket may break free into the heart, especially during laser transmission, which could result in a stroke. This removal also prevents the possibility of an electrical short between the aluminum jacket and the tip electrode, which could result in the patient receiving a lethally high voltage during laser transmission.

In another aspect of the invention, there is provided a DMR catheter having an infusion tube which extends from the proximal end of the catheter body through a lumen in the catheter body and into the tip section. The distal end of the infusion tube is open at the distal end of the tip section at a position adjacent the optic fiber so that fluids, including drugs to induce angiogenesis, may be passed through the catheter to the heart tissue. In a preferred embodiment, the DMR catheter comprises an infusion tube and a tip electrode having an infusion passage adjacent the optic fiber lumen. The infusion tube is connected to, preferably inserted into, the infusion passage in the tip electrode so that fluids passing through the infusion tube will enter and pass through the infusion passage in the tip electrode and to the heart tissue. The proximal end of the infusion tube terminates in a luer hub or the like.

In yet another aspect of the invention, the catheter body or shaft comprises a construction which exhibits improved torsional stability, resulting in improved tip control while minimizing wall thickness. The catheter body comprises a single central lumen and is formed by a tubular outer wall of polyurethane or nylon with a braided stainless steel mesh imbedded in the outer wall. The inner surface of the outer wall is lined with a stiffening tube, preferably made of polyimide or the like. The use of a polyimide stiffening tube provides improved torsional stability while at the same time minimizing the wall thickness of the catheter. This, in turn, maximizes the diameter of the central lumen. Such a construction is particularly useful in steerable DMR catheters in which an optic fiber, a puller wire, electrode leads, and an electromagnetic sensor cable all extend through the lumen of the catheter body, but is also useful in other steerable catheter constructions.

A preferred construction of the DMR catheter also includes a tubular spacer, between the polyimide stiffening tube and the tip section. The spacer is made of a material less stiff than the material of the stiffening tube, e.g., polyimide, but more stiff than the material of the tip section, e.g., polyurethane. Teflon® is the presently preferred material of the spacer.

In a preferred method for constructing the catheter, the stiffening tube is inserted into the tubular outer wall until the distal end of the stiffening tube butts against the tubular spacer. Force is applied to the proximal end of the stiffening tube which tube is then fixed in position, e.g., by glue, to the outer wall. The application of force on the proximal end of the stiffening tube assures that no gaps will form between the stiffening tube and tubular spacer or between the spacer and tip section as a result of repeated tip deflection.

In a steerable catheter construction comprising a stiffening tube and spacer, a puller wire preferably extends through a non-compressible compression coil which is fixed at its proximal end to the proximal end of the catheter body by means of a glue joint and fixed at its distal end to the proximal end of the tip section at a location distal to the spacer by means of a second glue joint. This arrangement prevents compression of the spacer during tip deflection which, in turn, permits the use of a thin walled spacer.

In yet another aspect to the invention, a control handle is provided which can be manipulated to deflect the tip section of the catheter. The control handle has a first member which is attached to the catheter body and a second member movable with respect to the first member, which is attached to the puller wire. In this arrangement, movement of the first member relative to the second member results in deflection of the tip. The handle comprises a guide tube through which the optic fiber extends. The guide tube is fixedly secured to the first or second member. Within this guide, the optic fiber is afforded lengthwise movement with respect to both the first and second members.

DESCRIPTION OF THE DRAWINGS

These and other features and advantages of the present invention will be better understood by reference to the following detailed description when considered in conjunction with the accompanying drawings wherein:

FIG. 1 is a side cross-sectional view of an embodiment of the catheter of the invention.

FIG. 2a is a side cross-sectional view of the catheter tip section showing an embodiment having three lumens and showing the position of the electromagnetic mapping sensor and the optic fiber.

FIG. 3 is a side cross-sectional view of the catheter body, including the junction between the catheter body and the tip section.

DETAILED DESCRIPTION

In a particularly preferred embodiment of the invention, there is provided a catheter for use in direct myocardial revascularization (DMR). As shown in FIGS. 1–4, catheter 10 comprises an elongated catheter body 12 having proximal and distal ends, a tip section 14 at the distal end of the catheter body 12, and a control handle 16 at the proximal end of the catheter body 12.

Figure 6:
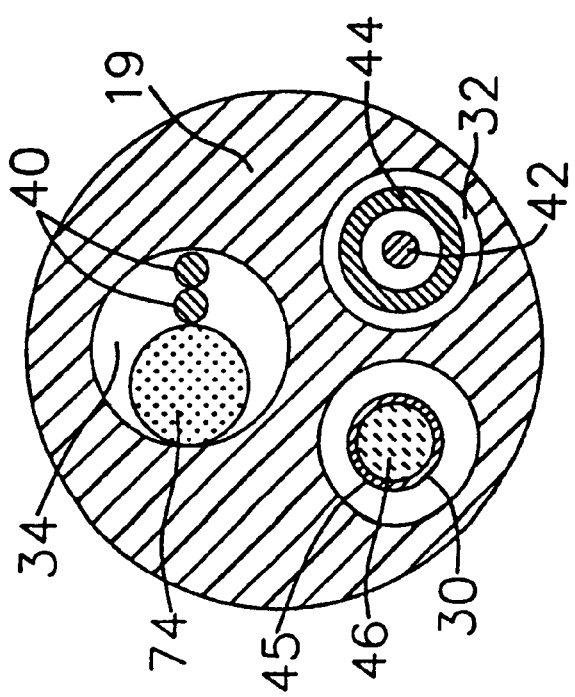
FIG. 6 is a transverse cross-sectional view of the catheter body along line 6—6.
Figure 5:
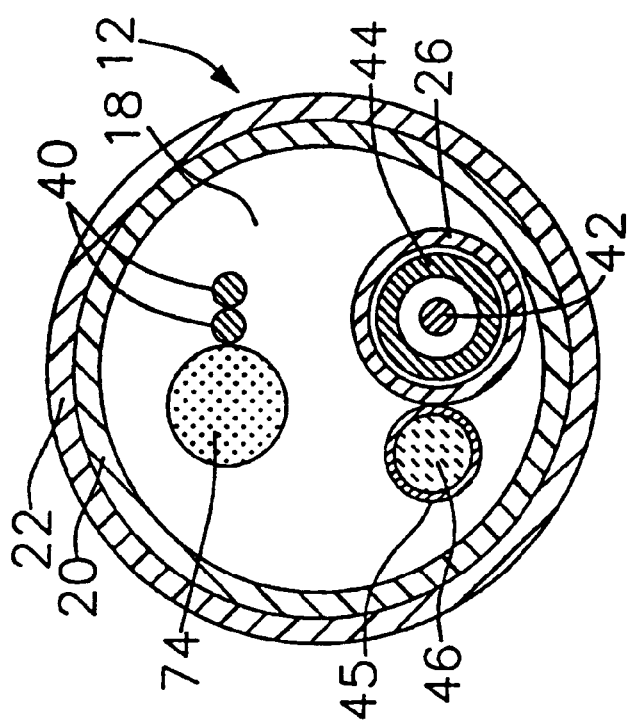
FIG. 5 is a transverse cross-sectional view of the catheter tip section along line 5—5 showing an embodiment having three lumens.

With reference to FIGS. 3 and 6, the catheter body 12 comprises an elongated tubular construction having a single, central or axial lumen 18. The catheter body 12 is flexible, i.e., bendable, but substantially non-compressible along its length. The catheter body 12 can be of any suitable construction and made of any suitable material. A presently preferred construction comprises an outer wall 22 made of a polyurethane or nylon. The outer wall 22 comprises an imbedded braided mesh of stainless steel or the like to increase torsional stiffness of the catheter body 12 so that, when the control handle 16 is rotated, the tip sectionally of the catheter 10 will rotate in a corresponding manner.

The outer diameter of the catheter body 12 is not critical, but is preferably no more than about 8 french. Likewise the thickness of the outer wall 22 is not critical. The inner wall 22, provides improved torsional stability while at the same time minimizing the wall thickness of the catheter, thus maximizing the diameter of the single lumen. The outer diameter of the stiffening tube 20 is about the same as or slightly smaller than the inner diameter of the outer wall 22. Polyimide tubing is presently preferred because it may be very thin walled while still providing very good stiffness. This maximizes the diameter of the central lumen 18 without sacrificing strength and stiffness. Polyimide material is typically not used for stiffening tubes because of its tendency to kink when bent. However, it has been found that, in combination with an outer wall 22 of polyurethane, nylon or other similar material, particularly having a stainless steel braided mesh, the tendency for the polyimide stiffening tube 20 to kink when bent is essentially eliminated with respect to the applications for which the catheter is used.

A particularly preferred catheter has an outer wall 22 with an outer diameter of about 0.092 inch and an inner diameter of about 0.063 inch and a polyimide stiffening tube having an outer diameter of about 0.0615 inch and an inner diameter of about 0.052 inch.

Figure 2B:
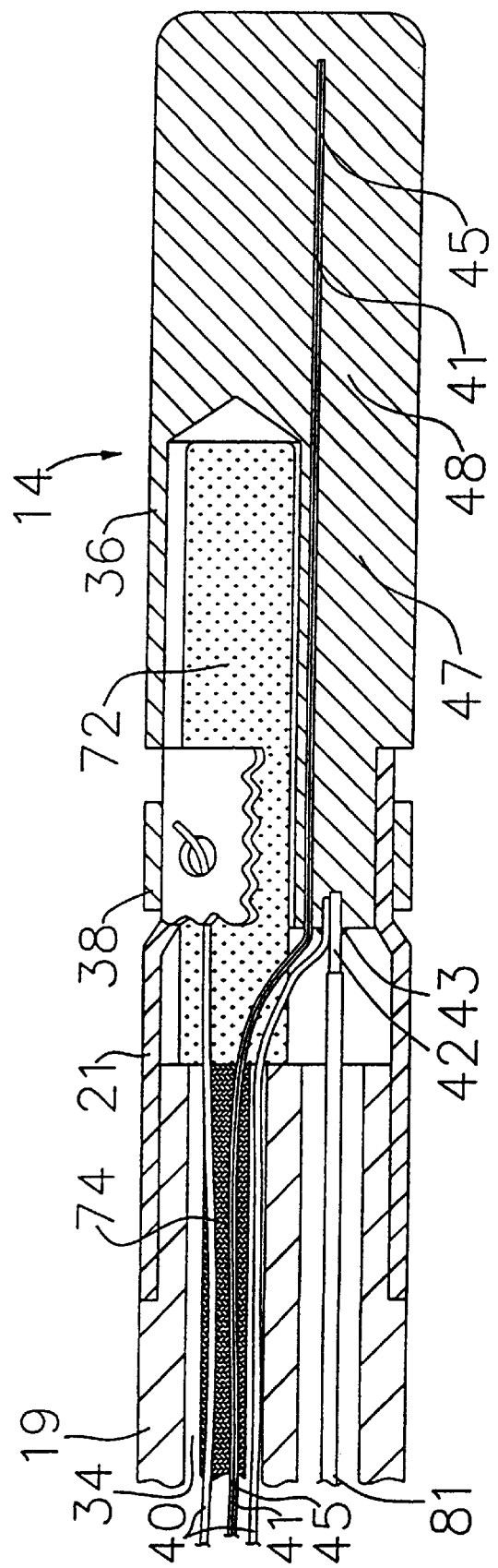
FIG. 2b is a side cross-sectional view of the catheter tip section showing an embodiment having three lumens and showing the position of the electromagnetic mapping sensor and the puller wire.

As shown in FIGS. 2a and 2b, the tip section 14 comprises a short section of tubing 19 having three lumens. The tubing 19 is made of a suitable non-toxic material which is preferably more flexible than the catheter body 12. A presently preferred material for the tubing 19 is braided polyurethane, i.e., polyurethane with an embedded mesh of braided stainless steel or the like. The outer diameter of the tip section 14, like that of the catheter body 12, is preferably no greater than about 8 french. The size of the lumens is not critical. In a particularly preferred embodiment, the tip section has an outer diameter of about 7 french (0.092 inch) and the first lumen 30 and second lumen 32 are generally about the same size, having a diameter of about 0.022 inch, with the third lumen 34 having a slightly larger diameter of about 0.036 inch.

A preferred means for attaching the catheter body 12 to the tip section 14 is illustrated in FIG. 3. The proximal end of the tip section 14 comprises an outer circumferential notch 24 that receives the inner surface of the outer wall 22 of the catheter body 12. The tip section 14 and catheter body 12 are attached by glue or the like. In the arrangement shown, a spacer 52 lies within the catheter body 12 between the distal end of the stiffening tube 20 and the proximal end of the tip section 14. The spacer 52 is preferably made of a material which is stiffer than the material of the tip section 14, e.g., polyurethane, but not as stiff as the material of the stiffening tube 20, e.g., polyimide. A spacer made of Teflon® is presently preferred. A preferred spacer 52 has a length of from about 0.25 inch to about 0.75 inch, more preferably about 0.5 inch. Preferably the spacer 52 has an outer and inner diameter about the same as the outer and inner diameters of the stiffening tube 20. The spacer 52 provides a transition in flexibility at the junction of the catheter body 12 and catheter tip 14, which allows the junction of the catheter body 12 and tip section 14 to bend smoothly without folding or kinking.

The spacer 52 is held in place by the stiffening tube 20. The stiffening tube 20, in turn, is held in place relative to the outer wall 22 by glue joints 23 and 25 at the proximal end of the catheter body 12. In a preferred construction of the catheter body 12, a force is applied to the proximal end of the stiffening tube 20 which causes the distal end of the stiffening tube 20 to firmly butt up against and compress the spacer 52. While under compression, a first glue joint is made between the stiffening tube 20 and the outer wall 22 by a fast drying glue, e.g. Super Glue®. Thereafter a second glue joint is formed between the proximal ends of the stiffening tube 20 and outer wall 22 using a slower drying but stronger glue, e.g., polyurethane. Construction of the catheter body 12 whereby the stiffening tube 20 and spacer 58 are under compression has been found to be advantageous to prevent the formation of gaps between the stiffening tube 20 and spacer 58 or between spacer 58 and the tip section 14 which might otherwise occur after repeated tip deflections. Such gaps are undesirable because they cause the catheter to crease or fold over, hindering the catheter's ability to roll.

Extending through the single lumen 18 of the catheter body 12 are lead wires 40, an optic fiber 46, a sensor cable 74, and a compression coil 44 through which a puller wire 42 extends. A single lumen 18 catheter body is preferred over a multi-lumen body because it has been found that the single lumen 18 body permits better tip control when rotating the catheter 10. The single lumen 18 permits the lead wires 40, the optic fiber 46, the sensor cable 74, and the puller wire 42 surrounded by the compression coil 44 to float freely within the catheter body. If such wires and cables were restricted within multiple lumens, they tend to build up energy when the handle 16 is rotated, resulting in the catheter body 12 having a tendency to rotate back if, for example, the handle is released, or if bent around a curve, to flip over, either of which are undesirable performance characteristics.

The puller wire 42 is anchored at its proximal end to the control handle 16 and anchored at its distal end to the tip section 14. The puller wire 42 is made of any suitable metal, such as stainless steel or Nitinol, and is preferably coated with Teflon® or the like. The coating imparts lubricity to the puller wire 42. The puller wire 42 preferably has a diameter ranging from about 0.006 to about 0.010 inches.

The compression coil 44 extends from the proximal end of the catheter body 12 to the proximal end of the tip section 14. The compression coil 44 is made of any suitable metal, preferably stainless steel. The compression coil 44 is tightly wound on itself to provide flexibility, i.e., bending, but to resist compression. The inner diameter of the compression coil 44 is preferably slightly larger than the diameter of the puller wire 42. For example, when the puller wire 42 has a diameter of about 0.007 inches, the compression coil 44 preferably has an inner diameter of about 0.008 inches. The Teflon® coating on the puller wire 42 allows it to slide freely within the compression coil 44. Along its length, the outer surface of the compression coil 44 is covered by a flexible, non-conductive sheath 26 to prevent contact between the compression coil 44 and any of the lead wires 40, optic fiber 46 or sensor cable 74. A non-conductive sheath 26 made of polyimide tubing is presently preferred.

The compression coil 44 is anchored at its proximal end to the proximal end of the stiffening tube 20 in the catheter body 12 by glue joint 29 and at its distal end to the tip section 14 at a location distal to the spacer 52 by glue joint 50. Both glue joints 29 and 50 preferably comprise polyurethane glue or the like. The glue may be applied by means of a syringe or the like through a hole made between the outer surface of the catheter body 12 and the single lumen 18. Such a hole may be formed, for example, by a needle or the like that punctures the wall of the catheter body 12 and the stiffening tube 20 which is heated sufficiently to form a permanent hole. The glue is then introduced through the hole to the outer surface of the compression coil 44 and wicks around the outer circumference to form a glue joint about the entire circumference of the compression coil 44.

The puller wire 42 extends into the second lumen 32 of the tip section 14. The puller wire 42 is anchored to a tip electrode 36 or to the side of the catheter tip section 14. With reference to FIGS. 2b and 3, within the tip section 14, and distal to the glue joint 51, the turns of the compression coil are expanded longitudinally. Such expanded turns 47 are both bendable and compressible and preferably extend for a length of about 0.5 inch. The puller wire 42 extends through the expanded turns 47 then into a plastic, preferably Teflon®, sheath 81, which prevents the puller wire 42 from cutting into the wall of the tip section 14 when the tip section 14 is deflected.

Figure 9:
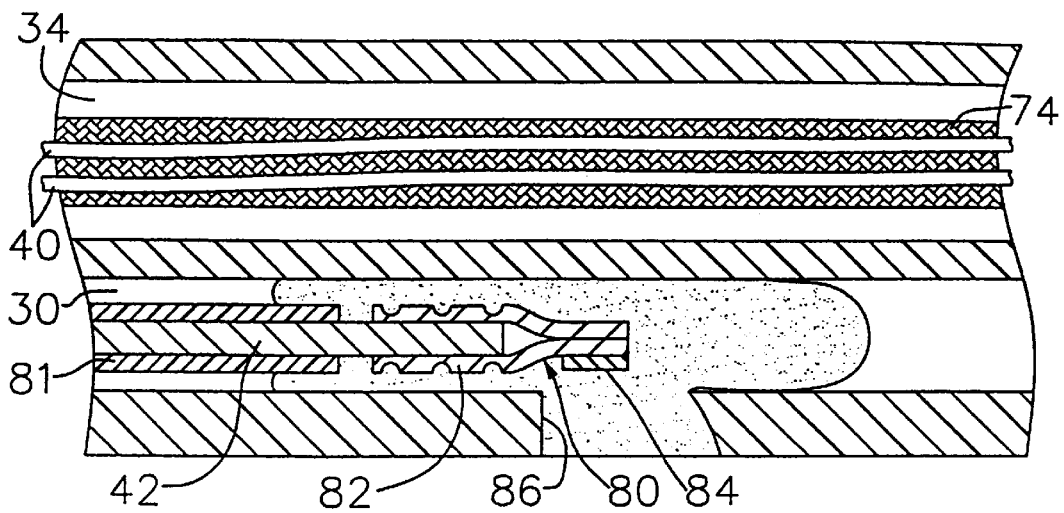
FIG. 9 is a cross-sectional view of a portion of the catheter tip section showing a preferred means for anchoring the puller wire.
Figure 10:
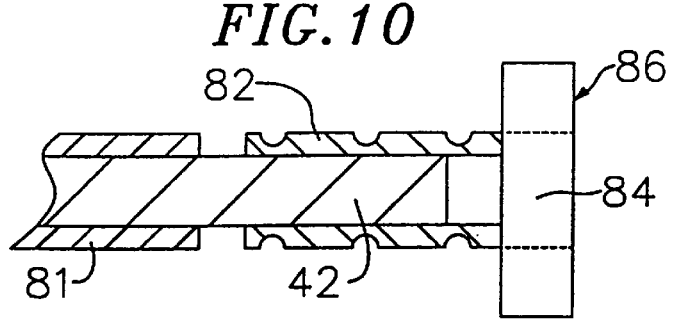
FIG. 10 is a top cross-sectional view of a preferred puller wire anchor.
Figure 11:
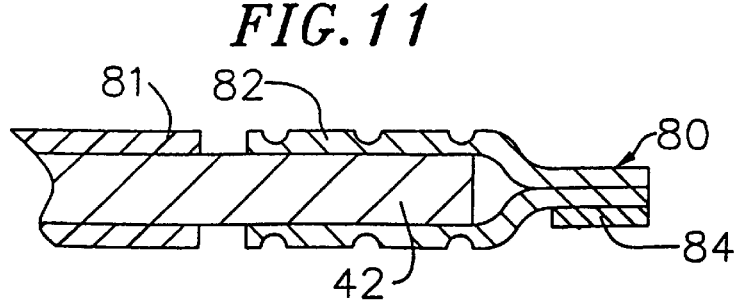
FIG. 11 is a side cross-sectional view of a preferred puller wire anchor.

The distal end of the puller wire 42 may be anchored to the tip electrode 36 by solder or the like, as shown in FIG. 2b or to the side wall of the tip section 14. If attached to the side wall, an embodiment comprising an anchor 80 fixedly attached to the distal end of the puller wire 42 is preferred, as illustrated in FIGS. 9–11. In such an embodiment, the anchor is formed by a metal tube 82, e.g., a short segment of hypodermic stock, which is fixedly attached, e.g., by crimping, to the distal end of the puller wire 42. The tube 82 has a section which extends a short distance beyond the distal end of the puller wire 42. A cross-piece 84 made of a small section of stainless steel ribbon or the like is soldered or welded in a transverse arrangement to the distal end of the tube 82, which is flattened during the operation. This creates a T-bar anchor 80. A notch 86 is created in the side of the catheter tip section 14 resulting in an opening into the second lumen 32 carrying the puller wire 42. The anchor 80 lies within the notch 86. Because the length of the ribbon forming the cross-piece 84 is longer than the diameter of the opening into the second lumen 32, the anchor 80 cannot be pulled completely into the second lumen 32. The notch 86 is then sealed with polyurethane or the like to give a smooth outer surface.

With reference to FIGS. 2a and 2b, at the distal end of the tip section 14 is a tip electrode 36. Preferably the tip electrode 36 has a diameter about the same as the outer diameter of the tubing 19. The tip electrode 36 is connected to the tubing 19 by means of a plastic housing 21, preferably made of polyetheretherketone (PEEK). The proximal end of the tip electrode 36 is notched circumferentially and fits inside the distal end of the plastic housing 21 and is bonded to the housing 21 by polyurethane glue or the like. The proximal end of the plastic housing 21 is bonded with polyurethane glue or the like to the distal end of the tubing 19 of the tip section 14.

Mounted on the distal end of the plastic housing 21 is a ring electrode 38. The ring electrode 38 is slid over the plastic housing 21 and fixed in place by glue or the like. If desired, additional ring electrodes may be used and can be positioned over the plastic housing 21 or over the flexible tubing 19 of the tip section 14.

The tip electrode 36 and ring electrode 38 are each connected to separate lead wires 40. The lead wires 40 extend through the third lumen 34 of tip section 14, the catheter body 12, and the control handle 16, and terminate at their proximal end in an input jack (not shown) that may be plugged into an appropriate monitor (not shown). If desired, the portion of the lead wires 40 extending through the catheter body 12, control handle 16 and proximal end of the tip section 14 may be enclosed or bundled within a protective tube or sheath.

The lead wires 40 are attached to the tip electrode 36 and ring electrode 38 by any conventional technique. Connection of lead wire 40 to the tip electrode 36 is preferably accomplished by weld 43, as shown in FIG. 2b. Connection of a lead wire 40 to a ring electrode 38 is preferably accomplished by first making a small hole through the plastic housing 21. Such a hole can be created, for example, by inserting a needle through the plastic housing 21 and heating the needle sufficiently to form a permanent hole. A lead wire 40 is then drawn through the hole by using a microhook or the like. The ends of the lead wire 40 are then stripped of any coating and soldered or welded to the underside of the ring electrode 38, which is then slid into position over the hole and fixed in place with polyurethane glue or the like.

In a particularly preferred embodiment of the invention, a temperature sensing means is provided for the tip electrode 36 and, if desired, the ring electrode 38. Any conventional temperature sensing means, e.g., a thermocouple or thermistor, may be used. With reference to FIG. 2b, a preferred temperature sensing means for the tip electrode 36 comprises a thermocouple formed by an enameled wire pair. One wire of the wire pair is a copper wire 41, e.g., a number 40 copper wire which acts not only as part of the thermocouple, but as the electrode lead. The other wire of the wire pair is a construction wire 45, e.g., a number 40 construction wire, which gives support and strength to the wire pair. The wires 41 and 45 of the wire pair are electrically isolated from each other except at their distal ends where they contact and are welded or soldered to the tip electrode 36. Because it is desirable to monitor the temperature of the tip electrode 36 at a site adjacent the distal end of the optic fiber 46, the thermocouple with a blind hole in the tip electrode 36 is fixed to the tip electrode 36 at the distal end of the blind hole as shown.

An optic fiber 46 for transmitting laser energy to create channels in the heart tissue slidably extends through the control handle 16 and catheter body 12 and into the first lumen 30 of the tip section 14. As used herein, "channels" refers to percutaneous myocardial channels that are formed in the heart tissue when the laser is fired. Preferred channels are approximately 1.0 millimeter in diameter and up to about 5.0 millimeters deep.

The distal end of the optic fiber 46 extends through an optic fiber lumen in the tip electrode 36 and is fixed to the tip electrode 36 by glue or the like. The distal end of the optic fiber 46 is flush with the distal surface of the tip electrode. A connector (not shown) at the proximal end of the optic fiber 46 can be used to connect the proximal end of the optic fiber 46 to a laser (not shown). Any suitable laser can be used. A presently preferred laser is a Shaplan Ho: YAG 2040 Laser.

The optic fiber 46 comprises a quartz core 48, a cladding made of doped silica or the like and a surrounding jacket 45. The jacket 45 can be of any suitable material, preferably aluminum, but materials such as such as nylon and polyimide may also be used. An aluminum jacket 45 is preferred as it tends to maximize the strength of the optic fiber 46 so that when the optic fiber is bent, e.g., when the catheter tip 14 is deflected, the quartz core does not break.

At the distal end of the optic fiber 46, the aluminum jacket 45 is stripped from the core 48. There are two principle reasons for this. The first is to prevent material from the aluminum jacket (or any other type of jacket) from breaking off into the heart chamber, particularly during laser transmission, which could lead to a stroke. The second is to electrically isolate the aluminum jacket 45 from the tip electrode 36. This is a safety measure to assure that a short circuit does not occur between the jacket 45 and tip electrode 36 that could deliver a potentially lethal burst of high voltage to the patient during laser transmission. A plastic, preferably polyimide, protective tube 47 is placed in surrounding relation to the portion of the optic fiber 46 covered by the jacket 45 that is situated within the tip electrode 36. The protective tube 47 prevents electrical contact between the jacket 45 and the tip electrode 36. The protective tube 47 extends beyond the distal end of the aluminum jacket 45 to help support the core 48. The protective tube 47 cannot extend too close to the distal tip of the optic fiber 46, however, because it would melt when the laser is fired. The protective tube 47 is fixed to the tip electrode 36 by glue or the like.

An electromagnetic sensor 72 is contained within the distal end of the tip section 14. The electromagnetic sensor 72 is connected by means of electromagnetic sensor cable 74, which extends through the third lumen 34 of the tip section 14 through the catheter body 12 into the control handle 16. The electromagnetic sensor cable 74 comprises multiple wires encased within a plastic covered sheath In the control handle 16, the wires of the sensor cable 74 are connected to a circuit board 64. The circuit board 64 amplifies the signal received from the electromagnetic sensor and transmits it to a computer in a form understandable by the computer. Also, because the catheter is designed for single use only, the circuit board contains an EPROM chip which shuts down the circuit board after the catheter has been used. This prevents the catheter, or at least the electromagnetic sensor, from being used twice. A suitable electromagnetic sensor is described, for example, in U.S. Pat. No. 4,391,199, which is incorporated herein by reference. A preferred electromagnetic mapping sensor 72 is manufactured by Biosense Ltd. Israel and marketed under the trade designation NOGA. To use the electromagnetic sensor 72, the patient is placed in a magnetic field generated, for example, by situating under the patient a pad containing coils for generating a magnetic field. A reference electromagnetic sensor is fixed relative to the patient, e.g., taped to the patient's back, and the DMR catheter containing a second electromagnetic sensor is advanced into the patient's heart Each sensor comprises three small coils which in the magnetic field generate weak electrical signals indicative of their position in the magnetic field. Signals generated by both the fixed reference sensor and the second sensor in the heart are amplified and transmitted to a computer which analyzes the signals and then displays the signals on a monitor. By this method, the precise location of the sensor in the catheter relative to the reference sensor can be ascertained and visually displayed. The sensor can also detect displacement of that catheter that is caused by contraction of the heart muscle.

Using this technology, the physician can visually map a heart chamber. This mapping is done by advancing the catheter tip into a heart chamber until contact is made with the heart wall. This position is recorded and saved. The catheter tip is then moved to another position in contact with the heart wall and again the position is recorded and saved.

The electromagnetic mapping sensor 72 can be used alone or more preferably in combination with the tip electrode 36 and ring electrode 38. By combining the electromagnetic sensor 72 and electrodes 36 and 38, a physician can simultaneously map the contours or shape of the heart chamber, the electrical activity of the heart, and the extent of displacement of the catheter and hence identify the presence and location of the ischemic tissue. Specifically, the electromagnetic mapping sensor 72 is used to monitor the precise location of the tip electrode in the heart and the extent of catheter displacement. The tip electrode 36 and ring electrode 38 are used to monitor the strength of the electrical signals at that location. Healthy heart tissue is identified by strong electrical signals in combination with strong displacement. Dead or diseased heart tissue is identified by weak electrical signals in combination with dysfunctional displacement, i.e., displacement in a direction opposite that of healthy tissue. Ischemic, or hibernating or stunned, heart tissue is identified by strong electrical signals in combination with impaired displacement Hence, the combination of the electromagnetic mapping sensor 72 and tip and ring electrodes 36 and 38 is used as a diagnostic catheter to determine whether and where use of the laser is appropriate. Once the presence and location of ischemic tissue has been identified, the DMR catheter can be deflected so that the optic fiber is normal, i.e., at a right angle, to the ischemic tissue, and laser energy is fired through the optic fiber in coordination with the heart activity, e.g. during systole, to create a channel in the ischemic tissue, for example, as described in U.S. Pat. Nos. 5,554,152, 5,389,096, and 5,380,316, the disclosures of which are incorporated herein by reference. This procedure is repeated to create multiple channels.

It is understood that, while it is preferred to include both electrophysiology electrodes and an electromagnetic sensor in the catheter tip, it is not necessary to include both. For example, a DMR catheter having an electromagnetic sensor but no electrophysiology electrodes may be used in combination with a separate mapping catheter system. A preferred mapping system includes a catheter comprising multiple electrodes and an electromagnetic sensor, such as the NOGA-STAR catheter marketed by Cordis Webster, Inc., and means for monitoring and displaying the signals received from the electrodes and electromagnetic sensor, such as the Biosense-NOGA system, also marketed by Cordis Webster, Inc.

The electrode lead wires 40, optic fiber 46 and electromagnetic sensor cable 74 must be allowed some longitudinal movement within the catheter body so that they do not break when the tip section 14 is deflected. To provide for such lengthwise movement, there are provided tunnels through the glue joint 50, which fixes the proximal end of the compression coil 44 inside the catheter body 12. The tunnels are formed by transfer tubes 27, preferably made of short segments of polyimide tubing. In the embodiment shown in FIG. 3, there are two transfer tubes 27 for the glue joint 50. Each transfer tube is approximately 60 mm long and has an outer diameter of about 0.021 inch and an inner diameter of about 0.019 inch. Extending through one transfer tube 27 are the lead wires 40 and the electromagnetic sensor cable 74. Extending through the other transfer tube 27 is the optic fiber 46.

An additional transfer tube 29 is located at the joint between the tip section 14 and the catheter body 12. Extending through this transfer tube is the optic fiber 46. This transfer tube 29 provides a tunnel through the glue joint formed when the tip section 14 is glued to the catheter body 12. It is understood that the number of transfer tubes may vary as desired.

Longitudinal movement of the puller wire 42 relative to the catheter body 12, which results in deflection of the tip section 12, is accomplished by suitable manipulation of the control handle 16. The distal end of the control handle 16 comprises a piston 54 with a thumb control 56 for manipulating the puller wire 42. The proximal end of the catheter body 12 is connected to the piston 54 by means of a shrink sleeve 28.

The optic fiber 46, puller wire 42, lead wires 40 and electromagnetic sensor cable 74 extend through the piston 54. The puller wire 42 is anchored to an anchor pin 36, located proximal to the piston 54. The lead wires 40 and electromagnetic sensor cable 74 extend though a first tunnel 58, located near the side of the control handle 16. The electromagnetic sensor cable 74 connects to the circuit board 64 in the proximal end of the control handle 16. Wires 80 connect the circuit board 64 to a computer and imaging monitor (not shown).

The optic fiber 46 extends through a guide tube 66, preferably made of polyurethane, and is afforded longitudinal movement therein. The polyurethane guide tube 66 is anchored to the piston 54, preferably by glue at glue joint 53. This allows the optic fiber 46 longitudinal movement within the control handle 16 so that it does not break when the piston 54 is adjusted to manipulate the puller wire 42. Within the piston 54, the puller wire 42 is situated within a transfer tube 27, and the electromagnetic sensor cable 74 and lead wires 40 are situated within another transfer tube 27 to allow longitudinal movement of the wires and cable near the glue joint 53.

The optic fiber 46 and guide tube 66 extend through a second tunnel 60 situated near the side of the control handle 16 opposite the anchor pin 36. To avoid undesirable bending of the optic fiber 46, a space 62 is provided between the proximal end of the piston 54 and the distal end of the second tunnel 60. Preferably the space 62 has a length of at least 0.50 inch and more preferably about from about 0.60 inch to about 0.90 inch.

In the proximal end of the control handle 16, the optic fiber 46 and the polyurethane guide tube 66 extend through a second larger plastic guide tube 68, preferably made of Teflon®, which affords the guide tube 66 and optic fiber 46 longitudinal slidable movement The second guide tube 68 is anchored to the inside of the control handle 16 by glue or the like and extends proximally beyond the control handle 16. The second guide tube 68 protects the fiber 46 both from contact with the circuit board 64 and from any sharp bends as the guide tube 66 and optic fiber 46 emerge from the control handle 16.

In another preferred catheter constructed in accordance with the present invention, there is provided an infusion tube 76 for infusing fluids, including drugs such as fibroblast growth factor (FGP), vaslar endothelial growth factor (VEGP), thromboxane-A2 or protein kinase-C. These are drugs that initiate or promote angiogenesis. FGP and VEGP work directly to initiate the formation of new blood vessels Thromboxane-A2 and protein kinase-C work indirectly to form new blood vessels. They are released by blood platelets during clot formation and have specific receptor sites which release FGF and VEGF.

Other preferred drugs tat may be infused include those which minimize the effect of foreign body reaction and extend the potency of the created channels. Drugs such as dexamethasone in various forms, e.g., dexamethasone sodium phosphate and dexamethasone acetate, can be delivered to sites to reduce inflammation associated with trauma and foreign body reaction which lead to the formation of fibrosis and collagen capsules which, in turn, close the created channels.

It is apparent that other drugs may be infused as desired. Moreover, saline, or the like, may be infused for controlling the temperature of the tip electrode. The infusion tube 76 may even be used for collecting tissue or fluid samples. The infusion tube 76 may be made of any suitable material, and is preferably made of polyimide tubing.

Figure 7:
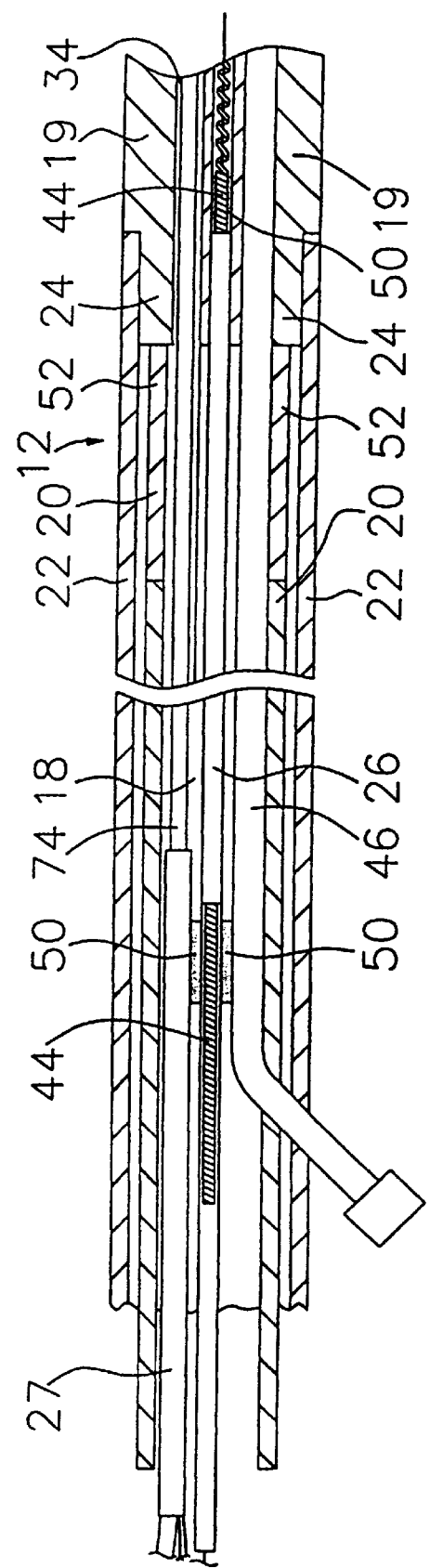
FIG. 7 is a side cross-sectional view of the catheter body showing an infusion tube.
Figure 8:
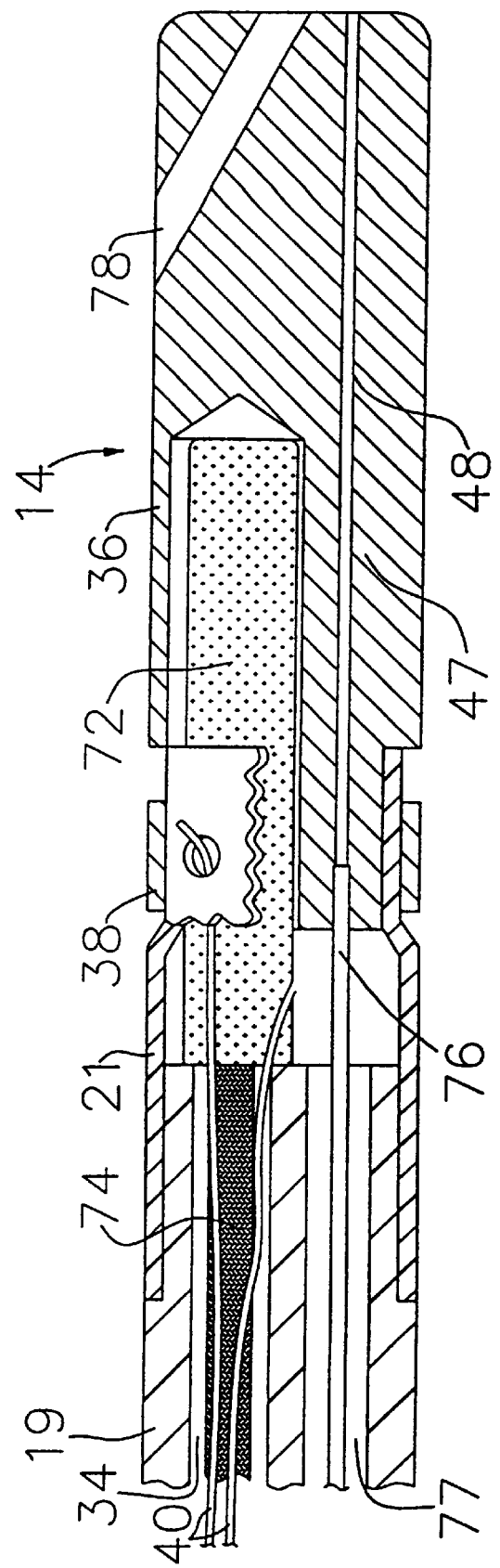
FIG. 8 is a transverse cross-sectional view of the catheter tip section showing an alternative embodiment having an infusion tube.

With reference to FIGS. 7 and 8, there is shown a catheter 10 having an infusion tube 76. The catheter 10 comprises a single lumen catheter body 12 as described above and a catheter tip section 14 comprising four lumens. To accommodate four lumens in the tip section, the diameter of the catheter may need to be increased slightly. The infusion tube 76 extends through the catheter body 12 and into the fourth lumen 77 of the tip section 14. The distal end of the infusion tube 76 extends into an opening or passage through the tip electrode 36 and is fixed, e.g., by glue, to the tip electrode 36. The passage in the tip electrode 36 may be straight or branched as desired. Alternatively, the infusion tube 76 can replace the optic fiber 46 in the first lumen 30 of the triple lumen tip section 14 in the embodiment described above.

The proximal end of the infusion tube 76 extends out of a sealed opening in the side wall of the catheter body and terminates in a luer hub or the like. Alternatively, the infusion tube 76 may extend through the control handle and terminate in a luer hub or the like at a location proximal to the handle. In this arrangement, fluids, including drugs to promote revascularization, may be infused into the heart at the precise location of the revascularization procedure.

In another embodiment, as shown in FIG. 8, a guide wire hole 78 is provided at the distal end of the tip section 14. The guide wire hole 78 extends from the side of the tip electrode 36 to the distal end of the tip electrode at an angle of about 30° to the longitudinal axis of the tip electrode. The guide wire hole 78 allows a guide wire (not shown) to be introduced into the heart and the catheter 10 to be passed over the guide wire until it is in the proper location within the heart. Generally, to get the guide wire into the heart, an introducing sheath is passed into the heart and then the guide wire is introduced into the heart from the introducing sheath.

In another preferred embodiment constructed in accordance with the present invention, two or more puller wires are provided to enhance the ability to manipulate the tip section. In such an embodiment, a second puller wire and a surrounding second compression coil extend through the catheter body and into separate off-axis lumens in the tip section. The lumens of the tip section receiving the puller wires may be in adjacent quadrants. The first puller wire is preferably anchored proximal to the anchor location of the second puller wire. The second puller wire may be anchored to the tip electrode or may be anchored to the wall of the tip section adjacent the distal end of tip section.

The distance between the distal end of the compression coils and the anchor sites of each puller wire in the tip section determines the curvature of the tip section 14 in the direction of the puller wires. For example, an arrangement wherein the two puller wires are anchored at different distances from the distal ends of the compression coils allows a long reach curve in a first plane and a short reach curve in a plane 90° from the first, i.e., a first curve in one plane generally along the axis of the tip section before it is deflected and a second curve distal to the first curve in a plane transverse, and preferably normal to the first plane. The high torque characteristic of the catheter tip section 12 reduces the tendency for the deflection in one direction to deform the deflection in the other direction.

As an alternative to the above described embodiment, the puller wires may extend into diametrically opposed off-axis lumens in the tip section. In such an embodiment, each of the puller wires may be anchored at the same location along the length of the tip section, in which case the curvatures of the tip section in opposing directions are the same and the tip section can be made to deflect in either direction without rotation of the catheter body.

Figure 4:
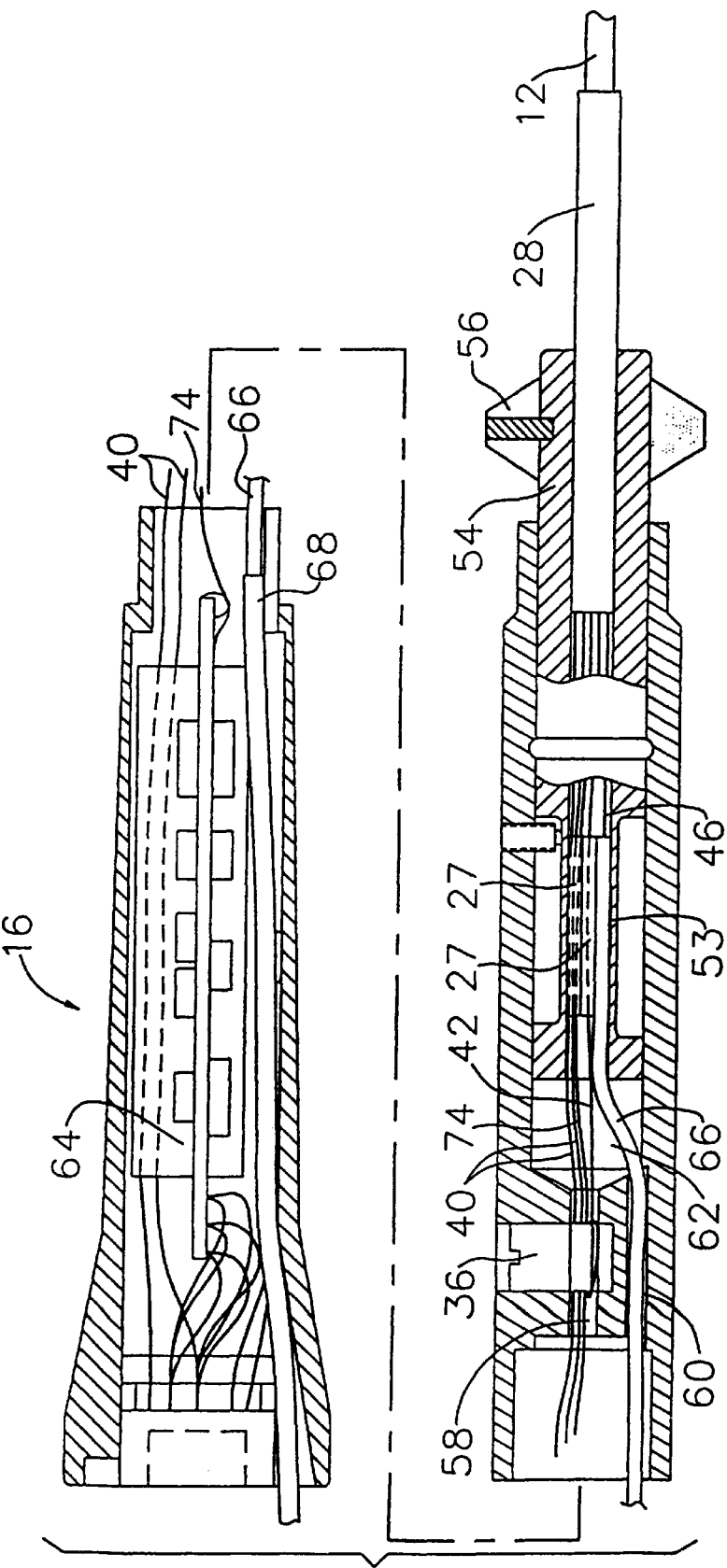
FIG. 4 is a side cross-sectional view of the catheter handle.

A particularly preferred catheter construction comprising multiple puller wires including control handle construction is disclosed in pending patent application entitled Omni-Directional Steerable Catheter, naming as inventor Wilton W. Webster, Jr. (attorney docket number 29963) filed concurrently herewith and incorporated hereby by reference. Such application describes a suitable control handle for manipulating two or more puller wires. The described control handle includes a central passage that may be expanded to accommodate the electrode lead wires, electromagnetic sensor cable, optic fiber and even infusion tube. Further, an extension of the handle may be provided to house the circuit bound for the electromagnetic sensor, e.g., in the same manner as shown in FIG. 4 herein.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

What is claimed is:

1. A steerable, direct myocardial revascularization catheter comprising:
   a catheter body having an outer wall, proximal and distal ends and at least one lumen extending therethrough;
   a control handle at the proximal end of the catheter body;
   a tip section comprising a flexible tubing having proximal and distal ends and at least one lumen extending therethrough, wherein the proximal end of the tip section is fixedly attached to the distal end of the catheter body;
   an electromagnetic sensor in the distal portion of the tip section for producing electrical signals indicative of the location of the electromagnetic sensor;
   an electromagnetic sensor cable electrically connected to the electromagnetic sensor and extending through the tip section, catheter body and control handle for carrying electrical signals from the electromagnetic sensor to a circuit board located in the control handle;
   an optic fiber having a distal end and a proximal end, said optic fiber extending through the control handle, a lumen in the catheter body and a lumen in the tip section, said distal end of the optic fiber being substantially flush with the distal end of the tip section; and
   means for deflecting the tip section by manipulation of the control handle.

2. A catheter according to claim 1 further comprising one or more electrodes carried by the tip section for mapping electrical activity of the heart tissue and one or more electrode lead wires electrically connected to each of the electrodes, said lead wires extending through a lumen in the tip section, a lumen in the catheter body and the control handle.

3. A catheter according to claim 2 comprising a tip electrode mounted at the distal end of the tip section, said tip electrode having a distal face and an optic fiber lumen therethrough.

4. A catheter according to claim 2 comprising one or more ring electrodes fixedly secured in surrounding relation to the tip section.

5. A catheter according to claim 3 comprising one or more ring electrodes fixedly secured in surrounding relation to the tip section.

6. A catheter according to claim 3 wherein the distal end of the optic fiber is fixedly secured within the optic fiber lumen of the tip electrode.

7. A catheter according to claim 1 wherein the circuit board is electrically attached to a cable, which is electrically attached to a computer for receiving signals from the circuit board.

8. A catheter according to claim 3 further comprising a tubular housing having distal and proximal ends, wherein the distal end of the tubular housing is fixedly attached to the proximal end of the tip electrode, wherein the proximal end of the tubular housing is fixedly attached to the distal end of the flexible tubing of the tip section.

9. A catheter according to claim 8 wherein the tubular housing is made of PEEK.

10. A catheter according to claim 1 wherein the catheter body has a single lumen extending therethrough.

11. A catheter according to claim 1 wherein the tip section has three lumens extending therethrough.

12. A catheter according to claim 1 wherein the outer wall comprises polyurethane or nylon.

13. A catheter according to claim 1, wherein the outer wall comprises an imbedded braided stainless steel mesh.

14. A catheter according to claim 12, wherein a braided stainless steel mesh is imbedded in the polyurethane or nylon.

15. A catheter according to claim 1 wherein the outer wall has an outer diameter of about 0.092 inch and an inner diameter of about 0.063 inch.

16. A catheter according to claim 1, wherein the catheter body further comprises an inner stiffening tube lining the outer wall, said stiffening tube having a distal end and a proximal end.

17. A catheter according to claim 16 wherein the stiffening tube comprises polyimide.

18. A catheter according to claim 16 wherein the stiffening tube has an outer diameter of about 0.0615 inch and an inner diameter of about 0.052 inch.

19. A catheter according to claim 16, further comprising a spacer between the distal end of the stiffening tube and the proximal end of the tip section.

20. A catheter according to claim 1 wherein the flexible tubing of the tip section is made of polyurethane.

21. A catheter according to claim 1 wherein the flexible tubing of the tip section comprises an imbedded braided stainless steel mesh.

22. A catheter according to claim 20 wherein the polyurethane tubing comprises an imbedded braided stainless steel mesh.

23. A catheter according to claim 1 wherein the control handle comprises a first member fixedly attached to the proximal end of the catheter body and a second member that is movable relative to the first member.

24. A catheter according to claim 23 wherein the deflecting means comprises a puller wire having a proximal end and a distal end, the puller wire extending from the control handle, through the catheter body and into the a lumen in the tip section, wherein the distal end of the puller wire is fixedly secured within the tip section and the proximal end of the puller wire is fixedly secured to the second member of the control handle, whereby manipulation of the first member of the control handle relative to the second member of the control handle moves the puller wire relative to the catheter body, resulting in deflection of the tip section.

25. A catheter according to claim 24 wherein the deflecting means further comprises a compression coil situated in the catheter body in surrounding relation to the puller wire and extending into a lumen in the tip section.

26. A catheter according to claim 25 wherein the compression coil is anchored to the catheter at the proximal end of the catheter body and at the proximal end of the tip section.

27. A catheter according to claim 1, further comprising an infusion tube having a proximal end and a distal end, said infusion tube extending through a lumen in the catheter body and a lumen in the tip section, wherein the distal end of the infusion tube is anchored in the tip section and wherein the proximal end of the infusion tube extends outside the catheter for receiving fluids.

28. A catheter according to claim 1, further comprising a temperature sensing means.

29. A catheter according to claim 28 wherein the temperature sensing means comprises a thermocouple formed by an enameled wire pair comprising a copper wire and a construction wire, wherein the enameled wire pair extends through a lumen in the catheter body and a lumen in the tip section and is fixedly attached in the distal end of the tip section.

* * * * *